United States Patent [19]

Sieverin

[11] 4,064,737

[45] Dec. 27, 1977

[54] LABORATORY STAND ASSEMBLY

[75] Inventor: Walter Joseph Sieverin, Buffalo Grove, Ill.

[73] Assignee: American Can Company, Greenwich, Conn.

[21] Appl. No.: 734,666

[22] Filed: Oct. 21, 1976

[51] Int. Cl.² .......................................... G01N 25/04
[52] U.S. Cl. .................................... 73/17 R; 23/292; 248/124
[58] Field of Search .................. 73/17 R, 36; 23/259, 23/292; 248/122-125

[56] References Cited

U.S. PATENT DOCUMENTS

| 2,001,004 | 5/1935 | Wantz | 248/124 |
| 2,486,685 | 11/1949 | Schneeman | 248/124 X |
| 2,535,855 | 12/1950 | Kurek | 73/17 |
| 2,682,765 | 7/1954 | McCutchan et al. | 73/36 |
| 3,392,945 | 7/1968 | Graham | 248/124 |

OTHER PUBLICATIONS

Precision Scientific Co. Bulletin 708 4/63.

Primary Examiner—Herbert Goldstein
Attorney, Agent, or Firm—Robert P. Auber; George P. Ziehmer; Ira S. Dorman

[57] ABSTRACT

A laboratory stand assembly includes a stand having a post, a sample holder bracket mounted on the post, a sample holder disengageably supported on the holder bracket, a probe mounting member adapted to support a probe, and a probe bracket mounted on the post which supports the probe member in both of two alternate positions. The stand assembly is especially suited for use in connection with the analysis of solder compositions, wherein a probe is inserted into a heated solder sample to monitor its cooling characteristics.

11 Claims, 4 Drawing Figures

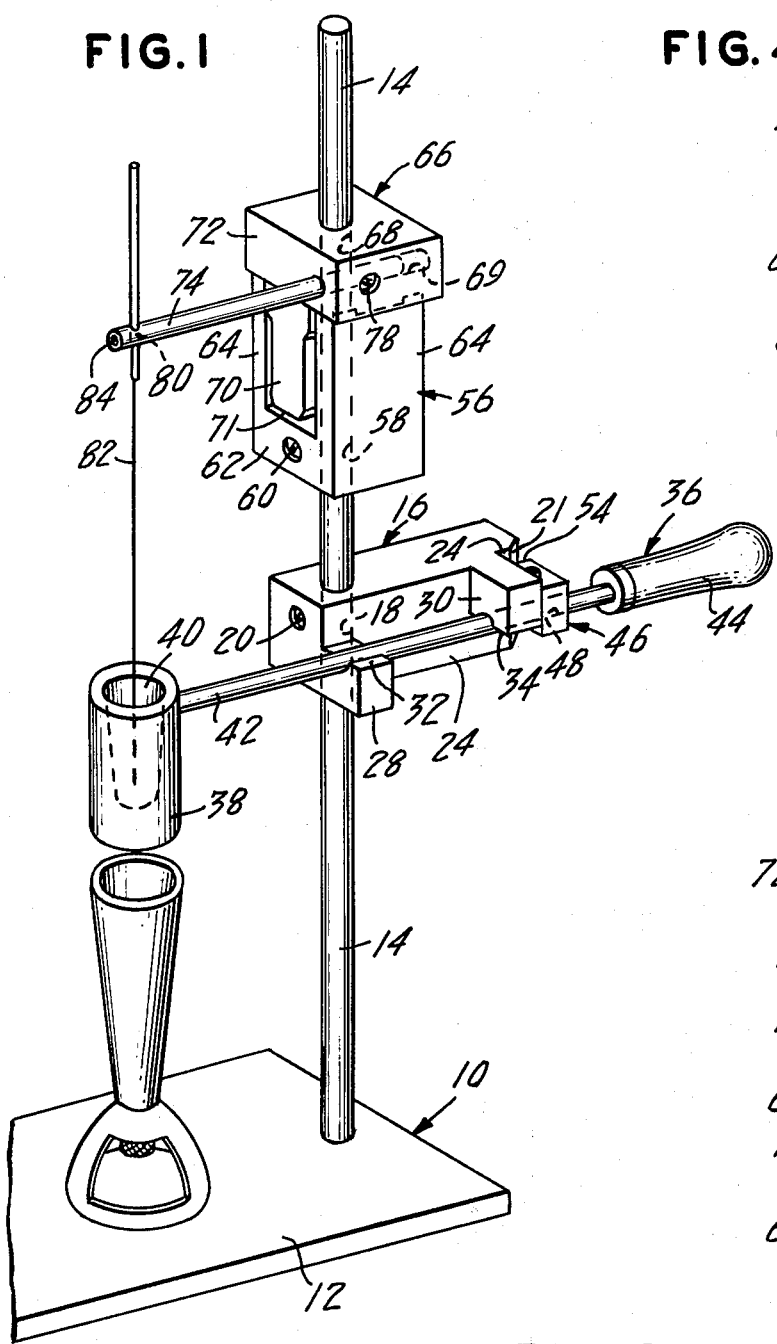
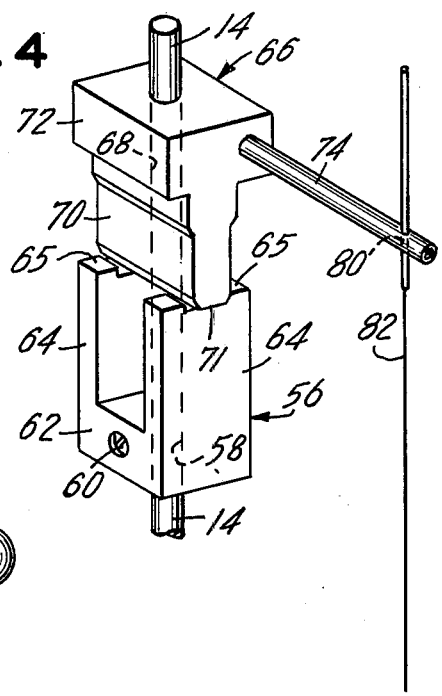
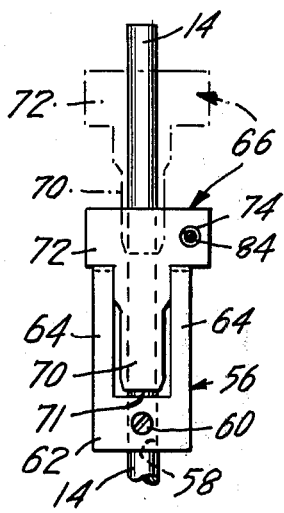
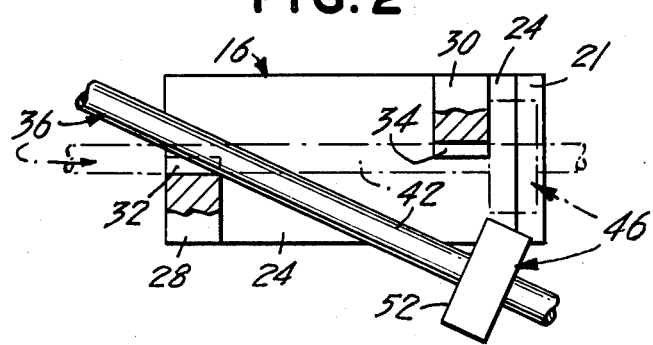

LABORATORY STAND ASSEMBLY

BACKGROUND OF THE INVENTION

Laboratory stand assemblies are, of course, well known in the art, and are widely used in industrial and research facilities. As a specific example, in the can manufacturing industry, such assemblies are used in connection with the analysis of the proportions of the lead and tin, or the lead, tin and silver components of the solder used to seal the side seam in three-piece cans. This is necessary to insure that an effective, but nonetheless, economical combination of components is achieved. Conventionally, a heat-sensitive probe is inserted into a small sample of heated solder to monitor its cooling characteristics. Since the freezing points, and/or phase changes of various combinations of metals are known, the specific component proportions of the solder sample can be easily determined and, in turn, any unacceptable deviation in the solder composition may then be corrected.

However, in order to achieve accurate measurements and to minimize test variables, it is essential that the immersion position and depth of the probe, relative to the solder sample, be the same in each test. Accordingly, for utmost reproducibility, a stand assembly is required which would minimize judgement and human error in the placement of the probe on each immersion. Moreover, for a practical commercial system, a stand assembly is required which is relatively inexpensive and simple to use and which, in particular, facilitates handling and mounting of the test sample and permits rapid and facile probe insertion and removal. Such an assembly, must also afford safeguards against the possibility of probe damage through improper handling. However, so far as is known, no presently-available stand assembly deals with these requirements in an entirely satisfactory and sufficiently simple manner.

Accordingly, it is an object of this invention to provide a novel laboratory stand assembly which permits accurate and reproducible test measurements.

It is also an object of this invention to provide such an assembly which facilitates the handling and mounting of test samples, and which facilitates accurate probe insertion and removal.

It is a further object of this invention to provide such an assembly which affords safeguards against the possibility of probe damage.

It is a more specific object of this invention to provide such a novel stand assembly which is especially adapted for use in connection with analysis of solder compositions.

It is another object of this invention to provide such a novel assembly which is relatively simple and inexpensive, durable and convenient to use.

SUMMARY OF THE INVENTION

It has now been found that certain of the foregoing and related objects are readily attained in an assembly including a stand with a post, the stand being adapted to support the post in a generally upright position; a sample holder bracket mounted on the post and having a pair of horizontally and vertically spaced lugs extending outwardly from one side thereof; and a sample holder having a sample-receiving portion and an elongated handle portion extending therefrom. The holder is disengageably supported on the holder bracket, adjacent the one side thereof, with the handle portion thereof engaged between the lugs of the bracket and constrained thereby against such pivotal movement as would permit downward movement of the receiving portion. Both the sample holder and also the holder bracket have means thereon which cooperate to constrain the receiving portion to a maximum spacing from the post, and both have means thereon which cooperate to prevent rotational movement of the holder about the axis of the handle portion thereof.

In certain embodiments, the "one" side of the holder bracket has a generally planar surface thereon, and the handle portion of the sample holder has a stop member mounted thereon. The stop member, in such embodiments, has a first surface which is disposed to engage the uppermost lug of the holder bracket, to constrain the receiving portion against axial shifting beyond the maximum spacing, and a second planar surface which is disposed to engage the planar surface of the one side of the bracket, to prevent rotational movement of the holder.

The assembly desirably includes means mounted on the post of the stand for supporting a probe, with at least a part of the supporting means being movable between a first position, with the probe adjacent the receiving portion of the sample holder, and a second position, with the probe withdrawn from the receiving portion. Normally, the sample receiving portion of the holder will have formed therein an upwardly opening cavity, into and from which the probe is inserted and withdrawn, respectively, in the aforesaid first and second positions of the supporting means.

In preferred embodiments, the supporting means comprises a probe mounting member having an arm extending therefrom, which is adapted to support the probe, and a probe bracket mounted on the post of the stand above the holder bracket, with the mounting member being movable between the first and second positions, and the probe bracket and mounting member being configured and dimensioned for cooperative support of the probe mounting member in both such positions. The second position is, most advantageously, rotatably displaced from the first position, about a generally vertical axis.

In particularly preferred embodiments, the probe mounting member is slidably mounted on the post of the stand and is of generally T-shaped configuration, with an upright leg and a generally transverse top beam extending thereacross. The probe bracket is of generally U-shaped configuration, with a transverse base beam and a side arm projecting upwardly from each end thereof. The probe member and bracket are dimensioned and configured so that, in the first position of the supporting means, the probe bracket supports the probe mounting member with the leg of the mounting member disposed between the side arms of the probe bracket, and with the top beam lying across the upper ends of the side arms and supported thereon. In the second position, the mounting member is rotated 90° about the vertical axis of the post, and the probe bracket supports the probe mounting member with the upright leg of the mounting member lying across and supported upon the upper ends of the side arms of the probe bracket. Desirably, the upper ends of the side arms of the bracket are transversely notched to receive the bottom end of the upright leg of the probe mounting member in the second position, and the upper portion of the upright leg of the probe member has a non-circular cross-section and is configured to closely mate with the channel of the bracket between the side arms thereof, to prevent rotational movement of the member when in the first position.

The bottom surface of the uppermost lug and the top surface of the lowermost lug may, advantageously, be transversely channeled to receive the handle portion of the holder. The sample-receiving portion of the sample holder may preferably comprise a crucible having a downwardly tapered cavity, with the crucible having a large mass relative to the sample to be analyzed. Finally, the sample holder, probe member and probe bracket are normally fabricated from metal.

BRIEF DESCRIPTION OF THE DRAWINGS

FIG. 1 is a perspective view of a novel laboratory stand assembly embodying the present invention;

FIG. 2 is a side elevational view of the sample holder bracket illustrated in FIG. 1, drawn to an enlarged scale therefrom, with portions broken away to show construction, and depicting, in full line, an initial stage of assembly of a fragmentarily illustrated sample holder and, in phantom line, its fully mounted position;

FIG. 3 is a front elevational view of the mounting member and probe bracket illustrated in FIG. 1, drawn to a slightly reduced scale therefrom, mounted on a fragmentarily-illustrated post and depicting, in full line, the probe member inserted within the channel of the probe bracket and, in phantom line, the probe member withdrawn from the channel of the probe bracket to effect a subsequent positional change; and FIG. 4 is perspective view of the probe member and probe bracket mounted on a fragmentarily-illustrated post, with a probe mounted on the arm of the probe member, drawn to a similar scale to that of FIG. 1, and showing the probe member rotatably displaced 90° about the post axis and in an alternate supported position on the probe bracket.

DETAILED DESCRIPTION OF THE ILLUSTRATED EMBODIMENT

Turning now in detail to the appended drawing, therein illustrated is a novel laboratory stand assembly embodying the present invention and including a stand, generally designated by the numeral 10, having a base 12 which supports a generally cylindrical, upright post 14. A sample holder bracket, generally designated by the numeral 16, is slidably mounted on the post 14 of the stand 10 by means of a bore 18 extending therethrough, and is held at a fixed height and angular orientation on the post 14 by means of a set screw 20. Extending outwardly from the planar surface 24 of the bracket 16 are lugs 28, 30, which are horizontally and vertically spaced from one another and have transverse channels in thier top and bottom surfaces, 32, 34, respectively; the bracket has a chamfer 21 along one edge, for a purpose to be discussed hereinbelow.

A sample holder, generally designated by the numeral 36, includes a generally cylindrical crucible 38, having formed therein an upwardly opened, downwardly tapered cavity 40. The crucible has a relatively large mass, compared to that of the test sample to be contained therein, so as to promote the uniform cooling of the solder sample, and its tapered cavity 40 permits ready removal of the sample after it has cooled. Extending laterally from the side of the crucible 38 is a generally cylindrical elongated shaft 42, the opposite end of which has a handle 44 attached thereto. As shown in FIG. 1, the sample holder 36 is disengageably supported on the sample holder bracket 16, with its shaft 42 engaged between the lugs 28, 30 of the bracket 16, and received within channels of their surfaces 32, 34. A stop member, generally designated by the numeral 46, of rectangular cross section is slidably mounted on the shaft 42 of the holder 36 by means of a bore 48 extending therethrough, and is held at a fixed axial position and angular orientation thereon by means of a set screw 50. The forward planar surface 52 of the stop member 46 abuts the rearward surface of the uppermost lug 30 to constrain the crucible 38 to a maximum spacing from the post 14. Additionally, a planar side surface 54 of the stop member 46 abuts the planar surface 24 of the one side of the bracket 16, to prevent rotation of the holder 36 about the axis of its shaft 42.

As is shown more clearly in FIG. 2, to effect placement of the holder 36 on the bracket 16, the crucible end of the holder 36 is tilted upwardly and its shaft 42 is positioned between the lugs 28, 30 and upon the channeled top surface 32 of the lower lug 28. The handle 44 of the holder 36 is then pivoted upwardly, about the lower lug 28, until the shaft 42 engages the upper lug 30, and is received within its channeled bottom surface 34. The holder 36 is then shifted axially until the stop member 46 contacts the uppermost lug 30 and planar surface 24 of the side of the bracket 16, with the chamfer 21 of the bracket 16 serving as an entry angle to facilitate engagement between the planar surface 54 of the stop member 46 and the planar surface 24 of the side of the bracket 16. As will be appreciated, the holder 36 is so balanced that the crucible end would cause it to pivot about the lug 28, were it not for the restraining effect of the lug 30, thus maintaining the holder 36 in a secure position therebetween. To effect disengagement, the handle 44 of the holder 36 is simply pivoted downwardly about the lowermost lug 28, thus elevating the crucible end and permitting withdrawal from between the lugs 28, 30.

A probe bracket, generally designated by the numeral 56, is slidably mounted on the post 14 of the stand 10 by means of a bore 58 extending therethrough, and is held at a fixed height and angular orientation thereon, above the sample bracket 16, by a set screw 60. The bracket 56 is of a generally U-shaped configuration, with a transverse base 62 and a side arm 64 projecting upwardly from each end thereof. The bracket 56 supports a probe member, generally designated by the numeral 66, which is slidably mounted on the post 14 of the stand thereabove by means of a bore 68 extending therethrough. As seen best in FIG. 1, the probe member 66 is of a generally T-shaped configuration, with an upright leg 70 and a transverse top beam 72 extending thereacross. The probe member 66 has an arm 74 extending laterally outward therefrom, slidably mounted in a bore 69 extending transversely through its top beam 72, and is held at a fixed axial position and angular orientation therein by means of a set screw 78. The outer end of the arm 74 has a bore 80 extending therethrough in which is supported, by means of a set screw 84 a vertically-disposed, fragmentarily-illustrated, thermocouple probe 82.

As can be seen by reference to FIGS. 1, 3 and 4, the probe member 66 may be supported on the probe bracket 56 in either of two alternate positions. In FIG. 1, the probe member 66 is supported with its upright leg 70 inserted between the side arms 64 of the bracket 56, and with its top beam 72 resting across the upper ends 65 of the side arms 64. As seen best in FIG. 3, the upper portion of the upright leg 70 is configured to closely mate with the channel of the probe bracket 56 between the side arms 64 thereof, thus preventing rotational movement of probe member 66, and the consequential possibility of damage to the probe 84 through impact on the crucible 38. The lower portion of the leg 70 is of reduced width to facilitate insertion of the probe member 66 into the channel of the bracket 56.

As will be noted, the sample holder bracket 16 and probe bracket 56 are spaced from one another in fixed axial positions and angular orientations on the post 14, and the crucible 38 and the probe 82 are disposed at fixed distances therefrom. As a result, in the position of FIG. 1, the tip of the probe 82 is disposed within, and axially aligned with, the cavity 40 of the crucible 38, so that the probe 82 will be immersed in the sample to be tested (not shown) at a predetermined depth and centralized position. As will be readily apparent, once the screw adjustments are set, the position and depth of the probe in the crucible cavity 40 will be the same, so long as the probe member 66 is supported on the probe bracket 56 in its lower position, and so long as the holder 36 is fully inserted in the bracket 16 with all intended surfaces in abutment.

To move the probe member 66 to the withdrawn position of FIG. 4, the probe member 66 is initially raised to clear the upper ends 65 of the side arms 64 of the probe bracket 56, it is rotated ninety degrees about the post 14, and it is finally lowered onto the bracket 56 with its upright leg 70 lying across and supported upon the upper ends 65 of the side arms 64 thereof. As will be noted the upper ends 65 of the side arms 64 are transversely notched to receive the bottom end 71 of the upright leg 70, and to constrain the probe member 66 against rotational movement, such as might permit it to slip back into the channel of the probe bracket 56, and thereby possibly cause damage to the probe 82. When the probe member 66 is in its elevated position, the sample holder may be readily removed from its associated bracket 16 without fear of interference with the probe 82.

While the instant assembly has been described in relation to the illustrated and preferred embodiment, it should be understood that modifications may be made, as will be apparent to those skilled in the art. For instance, while the stand assembly is especially useful in connection with the analysis of solder compositions, it may be used for a wide variety of testing procedures wherein the accurate positioning of test samples and test apparatus is of utmost importance. In addition, where the sample to be tested is of a nature which precludes use of the sample holder and bracket, the assembly may nevertheless be used to some advantage. It should also be noted that the positioning, angular orientation and configurations of the stand components will, of course, be modified to suit the particular test procedures and conditions involved. Finally, it will be appreciated that, while the stand components are typically fabricated from metal, other suitable materials, such as the various synthetic resins, may be used, and may be preferred in some instances.

Thus, it can be seen that the present invention provides a novel laboratory stand assembly which permits accurate and reproducible test measurements. The assembly facilitates the handling and mounting of test samples, and permits accurate and facile probe insertion and removal, while affording safeguards against the possibility of probe damage. The assembly is relatively simple and inexpensive to produce, and it is durable and convenient to use. In particular, the invention provides a novel stand assembly which is especially adapted for use in connection with the analysis of solder compositions.

What is claimed is:

1. A laboratory stand assembly, comprising: a stand having a post, and being adapted to support said post in a generally upright position; a sample holder bracket mounted on said post of said stand and having a pair of horizontally and vertically spaced lugs extending outwardly from one side thereof; and a sample holder having a sample-receiving portion and an elongated handle portion extending from said receiving portion, said holder being disengageably supported on said holder bracket, adjacent said one side thereof, with said handle portion thereof engaged between said lugs of said bracket and constrained thereby against pivotal movement, to prevent downward movement of said receiving portion, said sample holder and said holder bracket each having means thereon which cooperate to constrain said receiving portion to a maximum spacing from said post, and each having means thereon which cooperate to prevent rotational movement of said holder about the axis of said handle portion thereof.

2. The assembly of claim 1, wherein said one side of said holder bracket has a generally planar surface thereon, and wherein said handle portion of said sample holder has a stop member mounted thereon, said stop member having a first surface which is disposed to engage the uppermost lug of said holder bracket, to constrain said receiving portion against axial shifting beyond said maximum spacing, and having a second planar surface which is disposed to engage the planar surface of said one side of said bracket, to prevent rotational movement of said holder.

3. The assembly of claim 1, additionally including means mounted on said post of said stand for supporting a probe, at least a part of said supporting means being movable between a first position with the probe adjacent said receiving portion of said sample holder, and a second position with the probe withdrawn from said receiving portion.

4. The assembly of claim 3, wherein said sample receiving portion of said holder has formed therein an upwardly opening cavity, and wherein, in said first and second positions, the probe is inserted within and withdrawn from said cavity of said receiving portion of said holder, respectively.

5. The assembly of claim 4, wherein said supporting means comprises a probe mounting member having an arm extending therefrom which is adapted to support the probe, and a probe bracket mounted on said post of said stand above said holder bracket, said mounting member being movable between said first and second positions, and said probe bracket and mounting member being configured and dimensioned for cooperative support of said probe mounting member in both of said positions.

6. The assembly of claim 5, wherein said second position is rotatably displaced from said first position, about a generally vertical axis.

7. The assembly of claim 6 wherein said probe mounting member is slidably mounted on said post of said stand and is of generally T-shaped configuration, with an upright leg and a generally transverse top beam extending thereacross, and wherein said probe bracket is of generally U-shaped configuration, with a transverse base beam and a side arm projecting upwardly from each end thereof, said probe member and said bracket being dimensioned and configured so that, in said first position, said probe bracket supports said probe mounting member with said leg of said mounting member disposed between said side arms of said probe bracket and with said top beam lying across the upper ends of said side arms and supported thereon, and, in said second position, with said mounting member rotated 90° about the vertical axis of said post, said probe bracket supports said probe mounting member with said upright leg of said mounting member lying across and supported upon said upper ends of said side arms of said probe bracket.

8. The assembly of claim 7 wherein said upper ends of said side arms of said bracket are transversely notched to receive said bottom end of said upright leg of said probe mounting member in said second position, wherein the upper portion of said upright leg of said probe member has a non-circular cross-section and is configured to closely mate with said channel of said bracket between said side arms thereof, to prevent rotational movement of said member when in said first position, and wherein the bottom surface of said uppermost lug and the top surface of the lowermost lug are transversely channeled to receive said handle portion of said holder.

9. The assembly of claim 8 wherein said sample-receiving portion of said sample holder comprises a crucible having a downwardly tapered cavity, said crucible having a large mass relative to the sample to be analyzed.

10. The assembly of claim 9 wherein said sample holder bracket, said probe member and said probe bracket are fabricated from metal.

11. A laboratory stand assembly, comprising: a stand having a post, and being adapted to support said post in a generally upright position; a probe mounting member having an arm extending therefrom which is adapted to support a probe, said mounting member being slidably mounted on said post of said stand and being of generally T-shaped configuration, with an upright leg and a transverse top beam extending thereacross; and a probe bracket fixedly mounted on said post of said stand beneath said mounting member, said bracket being of generally U-shaped configuration with a transverse base beam and a side arm projecting upwardly from each end thereof, said probe bracket and mounting member being dimensioned and configured for cooperative support of the probe in first and second positions, with said probe bracket supporting said probe mounting member in said first position with said leg of said mounting member disposed between said side arms of said probe bracket and said top beam lying across the upper ends of said side arms and supported thereon, and said probe bracket supporting said probe mounting member in said second position with said mounting member rotated 90° about the vertical axis of said post and with said upright leg of said mounting member lying across and supported upon said upper ends of said side arms of said probe bracket.

\* \* \* \* \*